United States Patent [19]
Schroder et al.

[11] Patent Number: 5,968,541
[45] Date of Patent: Oct. 19, 1999

[54] COMPOSITION AND METHOD FOR THE CONTROL OF DIABROTICITE INSECTS

[75] Inventors: Robert F. W. Schroder, Westminster; Albert B. Demilo, Bowie, both of Md.; Chang Joo Lee, Taejeon, Rep. of Korea

[73] Assignee: The United States of America, as represented by the Secretary of Agriculture, Washington, D.C.

[21] Appl. No.: 08/917,852

[22] Filed: Aug. 27, 1997

[51] Int. Cl.⁶ .............................. A01N 25/00; A01N 43/16
[52] U.S. Cl. ........................ 424/405; 514/454; 514/455
[58] Field of Search ........................... 424/405; 514/455, 514/454

[56] References Cited

U.S. PATENT DOCUMENTS

| | | |
|---|---|---|
| 4,565,695 | 1/1986 | Guss et al. . |
| 4,647,578 | 3/1987 | Crounse et al. ................. 514/454 |
| 4,983,390 | 1/1991 | Levy ................................ 424/404 |
| 5,091,183 | 2/1992 | Yano et al. ..................... 424/405 |
| 5,464,618 | 11/1995 | Doane et al. . |
| 5,571,522 | 11/1996 | Munson et al. . |
| 5,676,959 | 10/1997 | Heitz et al. .................... 424/405 |

OTHER PUBLICATIONS

Metcalf et al., *Proc. Natl. Acad. Sci. USA*, vol. 77(7), pp. 3769–3772 (1980).
Lance et al., *J. Econ. Entomology*, vol. 85(3), pp. 967–973 (1992).
Metcalf et al., *J. Econ. Entomology*, vol. 80(4), pp. 870–875 (1987).
Peterson et al., *J. Econ. Entomology*, vol. 78(4), pp. 738–741 (1985).
James R. Heitz, *Xanthene Dyes as Pesticides*, Insecticide Mode of Action, copyright 1982 by Academic Press, Inc., pp. 429–457.

*Primary Examiner*—Jose' G. Dees
*Assistant Examiner*—Alton Pryor
*Attorney, Agent, or Firm*—M. Howard Silverstein; John D. Fado; Janelle S. Graeter

[57] ABSTRACT

Diabroticite insects, in particular the corn rootworm, are major pests of corn as well as a variety of other agricultural crops. The invention describes an aqueous composition which is effective as an insectide for the control of Diabroticite insects and contains a photoactive xanthene dye, such as phloxine B, as a toxicant and a cucurbitacin-containing feeding stimulant. Additives such as a starch thickener and an adherent may also be included in the composition.

18 Claims, 6 Drawing Sheets fig. 1 fig. 2a fig. 2b fig. 3 fig. 4 fig. 5

COMPOSITION AND METHOD FOR THE CONTROL OF DIABROTICITE INSECTS

BACKGROUND OF THE INVENTION

1. Field of the Invention

The corn rootworm (CRW) is a major threat to the production of corn in North America. Costs associated with attempts to control the pest combined with monetary losses due to crop damage can exceed $1 billion per year. Moreover, the CRW causes an additional $100 million in damage and control costs on cucurbits, peanuts and soybeans; adult insects have caused considerable damage to many fruits and have been implicated as carriers of some plant diseases as well.

Chemical pesticides for the control of the CRW pest complex are applied to 12–16 million hectares per year. These chemicals often have been applied as a preventive measure, sometimes unnecessarily, thus increasing the health risks imposed on the general population as well as on livestock and other farm and domestic animals and wildlife.

The need for an effective agent for the control of CRW which is also environmentally safe is thus well-established. This invention relates to a toxicant-bait formulation effective for controlling corn rootworm and to its method of use.

2. Description of the Relevant Art

An interesting relationship between insect herbivores and their host plants is the phenomenon exhibited by insects feeding compulsively on phytochemicals that are toxic to other insects. This phenomenon occurs between CRW and their ancestral plant hosts, the Curbitaceae. These plants produce very bitter compounds, cucurbitacins, which are phagostimulants for many of the CRW pest species (Metcalf, R. L. 1986. *J. Chem. Ecol.* vol. 12, pp. 1109–1124; Metcalf and Lampman. 1989. *J. Econ. Entomol.* vol. 82, pp. 1620–1625; Tallamy and Kriachik. 1989. *Amer. Nat.* vol. 133, pp. 766–786; Metcalf and Rhodes. 1990. In: *Biology and utilization of the cucurbitaceae*. Bates et al., eds. Comstock, Ithaca, N.Y.). No evidence of acute toxicity exhibited by the compounds has been produced (Tallamy and Halaweish. 1993. *Environ. Entomol.* vol. 22, pp. 925–932).

There has been a major effort to replace ineffective and environmentally undesirable soil insecticides with baits laced with cucurbitacins and toxins (Metcalf et al. 1987. *J. Econ. Entomol.* vol. 80, pp. 870–875; Lance, D. R. 1988. *J. Econ. Entomol.* vol. 81, pp. 1359–1362; Weissling et al. 1989. *Entomol. Exp. Appl.* vol. 53, pp. 219–228; Lance and Sutter. 1990. *J. Econ. Entomol.* vol. 83, pp. 1085–1090; Lance and Sutter. 1991. *J. Econ. Entomol.* vol. 84, pp. 1861–1868; Weissling and Meinke. 1991. *Environ. Entomol.* vol. 20, pp. 945–952; Brust and Foster. 1995. *J. Econ. Entomol.* vol. 88, pp. 112–116). Lacing the baits with cucurbitacins causes the beetles to compulsively feed on them, and they die from the insecticides present in the composition. The increased feeding brought on by the presence of the cucurbitacins has resulted in a reduction in the amount of insecticide necessary for an effective formulation by 90–95%. These baits are pest specific and are capable of killing 99% of the beetles consuming them (Tallamy and Halaweish, supra). Carbaryl, a semiochemical-based insecticide bait specific to CRW, for example, has been developed by a research team comprised of entomologists from USDA, ARS, universities, and industry (Chandler et al. 1995. In: *Clean water, clean environment. 21st centure team agriculture, working to protect water resources*. Conf. Proceed. vol. 1, pp. 29–32) and is currently under commercial development. The baits are currently being evaluated in areawide Integrated Pest Management (IPM) programs for CRW control on limited corn acreage in the Corn Belt (Chandler et al., supra).

The goal of agronomists in refining IPM practices is to rely less on synthetic chemicals in baits and, if possible, to find other approaches to managing the CRW (Butler, R. E. 1992. *Seed World*. vol. 130, pp. 8–10). Various attempts have therefore been made to develop formulations effective for controlling corn rootworm. The baits laced with insecticides and feeding stimulants, e.g. those reported by Metcalf et al., supra, are prepared from Cucurbita fruits which were dried, ground and impregnated with insecticides and volatile attractants. These baits were then scattered over plots of sweet corn, with some of the bait on the leaves and silks of the ears of corn. Lance and Sutter (1992. *J. Econ. Entomol.* vol. 85, pp. 967–973) also described a bait formulation containing an insecticide, a feeding stimulant and volatile attractants. In both instances, volatile attractants were included since cucurbitacins, although recognized as powerful feeding stimulants, are not effective as attractants. Delivery of the insecticide was therefore accomplished by first attracting the insect, then stimulating it to feed on the insecticide-laced bait.

Other compositions and methods have also been utilized in attempts to control the corn rootworm. Guss et al. (U.S. Pat. No. 4,565,695, 1986) suggest the use of synthetic pheromone for mating disruption or for use in combination with larval insecticides. Doane et al. (U.S. Pat. No. 5,464,618, 1995) describe a gustatory stimulant comprising dried and powdered plant material containing cucurbitacins, a lubricant and an adherent to be used in combination with an insecticide for adult beetles. Munson et al. (U.S. Pat. No. 5,571,522, 1996) describe a feeding stimulant to be used in combination with an insecticide where the feeding stimulant is corn germ.

All these various approaches have suffered from a lack of consistency in the delivery of the insecticide to the targeted insect. While cucurbitacins are potent feeding stimulants, they do not serve as attractants at all, so the targeted pests must be in the immediate vicinity of the compounds in order for them to be effective. Dry formulations have thus resulted in a substantial portion of the insecticide being wasted because it is never consumed. This waste is deleterious not only because of cost and ineffectiveness, but also because it results in insecticide remaining in the fields to contaminate the soil, ground water and other sources of water such as lakes, rivers and streams.

SUMMARY OF THE INVENTION

We have now discovered a composition which is consistently effective for the control of corn rootworm and at the same time is environmentally safe. The composition comprises cucurbitacin feeding stimulants and a toxicant in aqueous solution, where the toxicant comprises water-soluble, photoactive xanthene-type dyes.

In accordance with this discovery, it is an object of the invention to provide a composition for the control of Diabroticite insects, such as corn rootworm.

It is also an object of the invention to provide a method of controlling corn rootworm by applying the composition in amounts effective for reducing the population of Diabroticite insects, such as corn rootworm.

Other objects and advantages of the invention will become readily apparent from the following description.

BRIEF DESCRIPTION OF THE DRAWINGS

FIG. 2 shows the effects of varying concentrations of dye on SCR mortality both with feeding stimulant (FIG. 2a) and without feeding stimulant (FIG. 2b).

DETAILED DESCRIPTION OF THE INVENTION

The corn rootworm pest complex (subfamily Galerucinae) is comprised of two taxonomic groups, Virgifera and Fucata. The Virgifera group beetles overwinter as eggs in the soil and are univoltine. This group is comprised of northern corn rootworm (NCR), *Diabrotica longicornis barberi* Smith & Lawrence, from the upper Mississippi Valley; western corn rootworm (WCR), *D. virgifera virgifera* LeConte, from the Midwestern U.S.; and Mexican corn rootworm (MCR), *D.v. zeae* Krysan & Smith, from the south central U.S.

The Fucata group beetles overwinter as adults and are multivoltine. They include the western spotted cucumber beetle (WSCB), *D. undecimpunctata undecimpunctata* Mannerheim, ranging from the far western U.S. into the upper Baja Peninsula; the banded cucumber beetle (BCB), *D. balteata* LeConte, from the southeast U.S.; and the southern corn rootworm (SCR), *D.u. howardi* Barber, commonly known as the spotted cucumber beetle in the adult stage and ranging east of the rockies from southern Canada into Mexico.

Both larvae and adults are responsible for extensive feeding damage. For example, larvae of SCR hatch from eggs of overwintering adults and either feed on seedling corn roots or bore into the base of the stem. They also attack peanut crops by penetrating the developing peanut and either consuming it or facilitating attack by disease-causing microorganisms.

After feeding, diabroticine larvae pupate and emerge from the ground as adult beetles. Multivoltine species (e.g. SCR) can produce up to three generations a year. The univoltine beetle (e.g. NCR and WCR) life cycle begins with eggs laid below the surface of the soil in the fall. In early spring, the larvae hatch and begin to feed. Beetles emerge from mid-July through August, with male beetles emerging about 1 week before the females.

Attempts have been made to control CRW in both the larval and adult stages with dry formulations, but this approach has generally been problematic with respect to actual delivery of insecticide to the targeted pest. In order for the insecticide to be effective, it must be ingested in sufficient amounts to kill the insect and enough of the targeted insects must ingest enough insecticide in order to reduce, i.e. control, the insect populations to tolerable levels. In order to overcome this problem, investigations were carried out on aqueous-based toxicant-bait formulations which could be applied more uniformly on plants where beetles were more active and feeding would be preferred.

Figure 1:
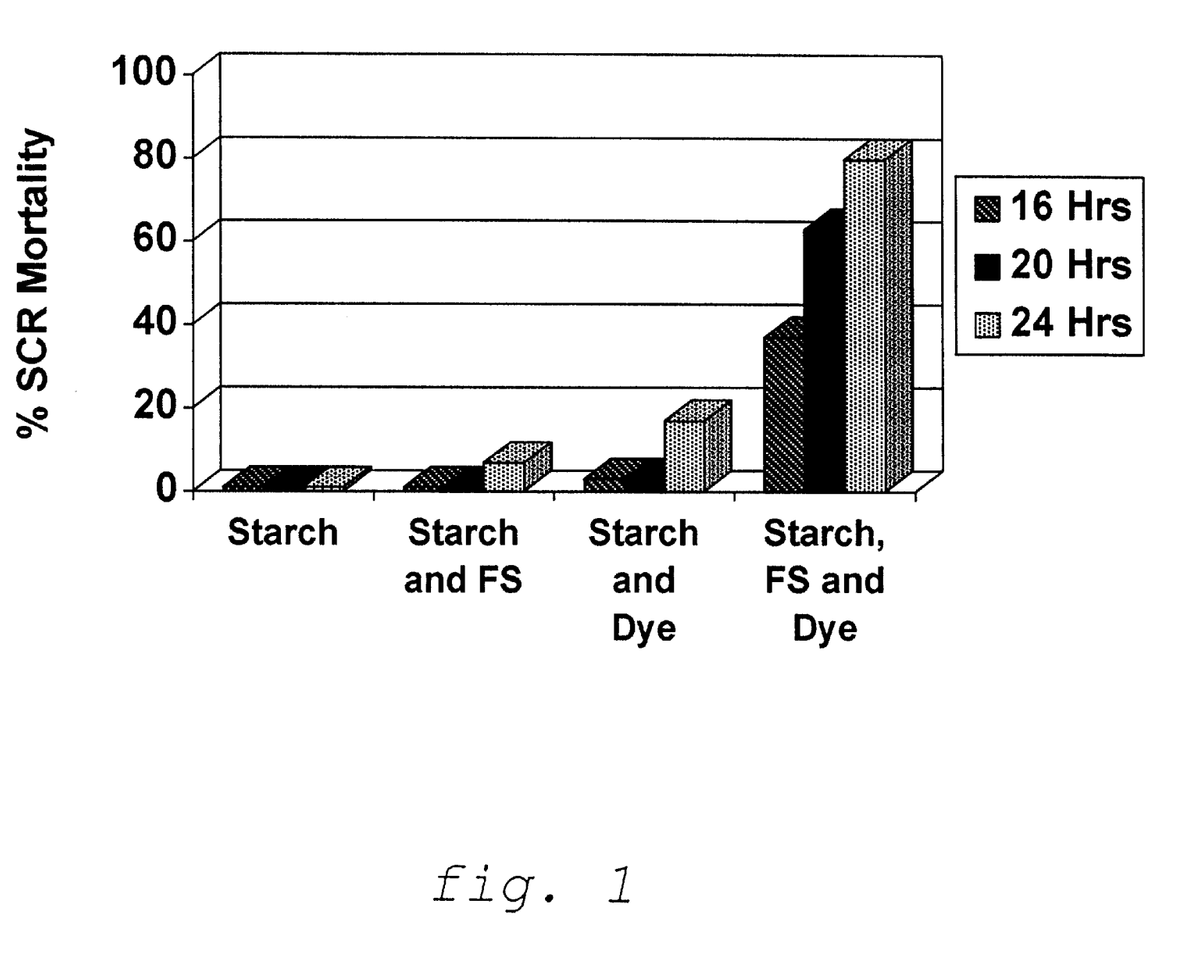
FIG. 1 shows the effects of the various components of the composition on southern corn rootworm (SCR) mortality.
Figure 2A:
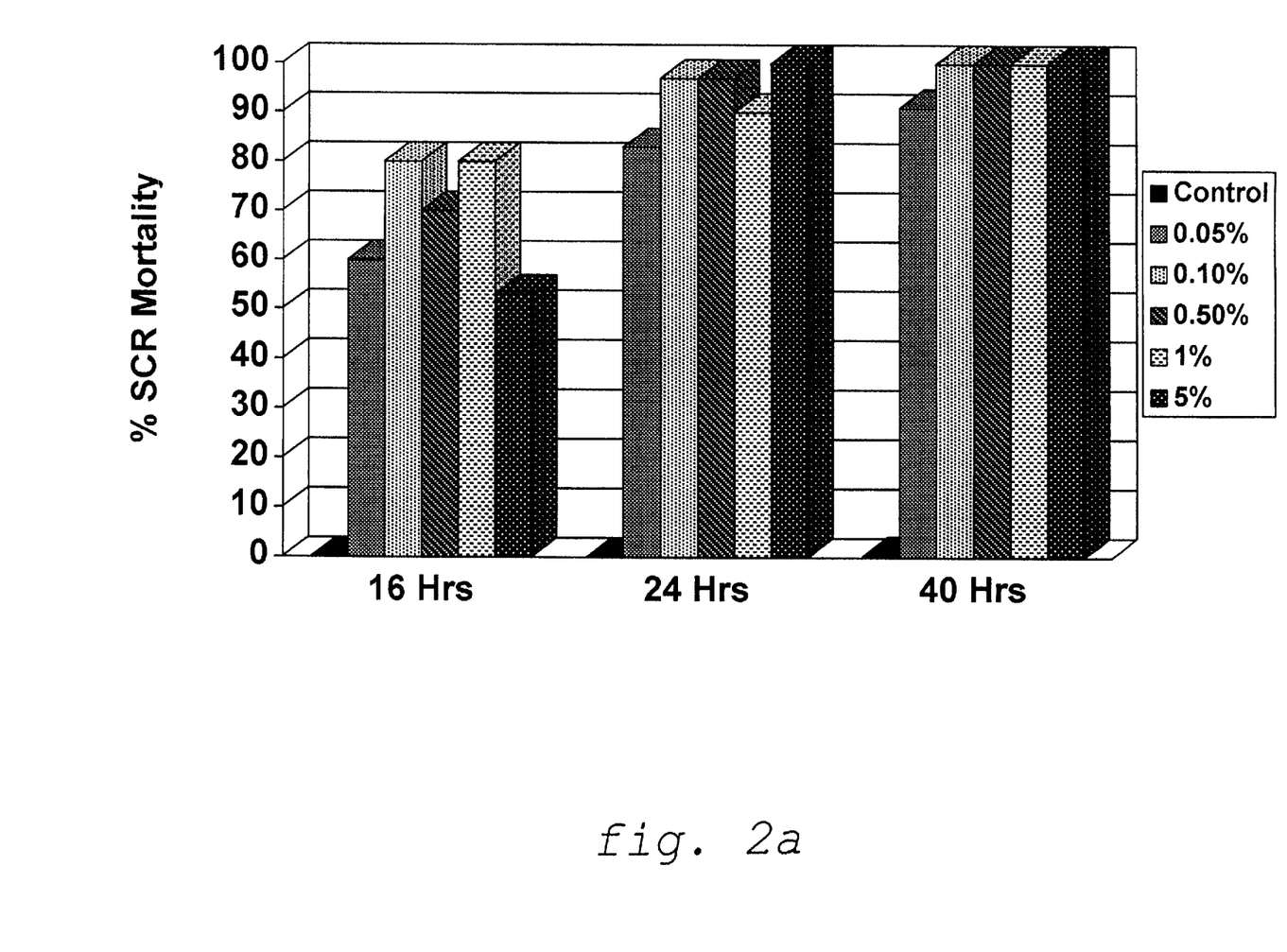
Figure 2B:
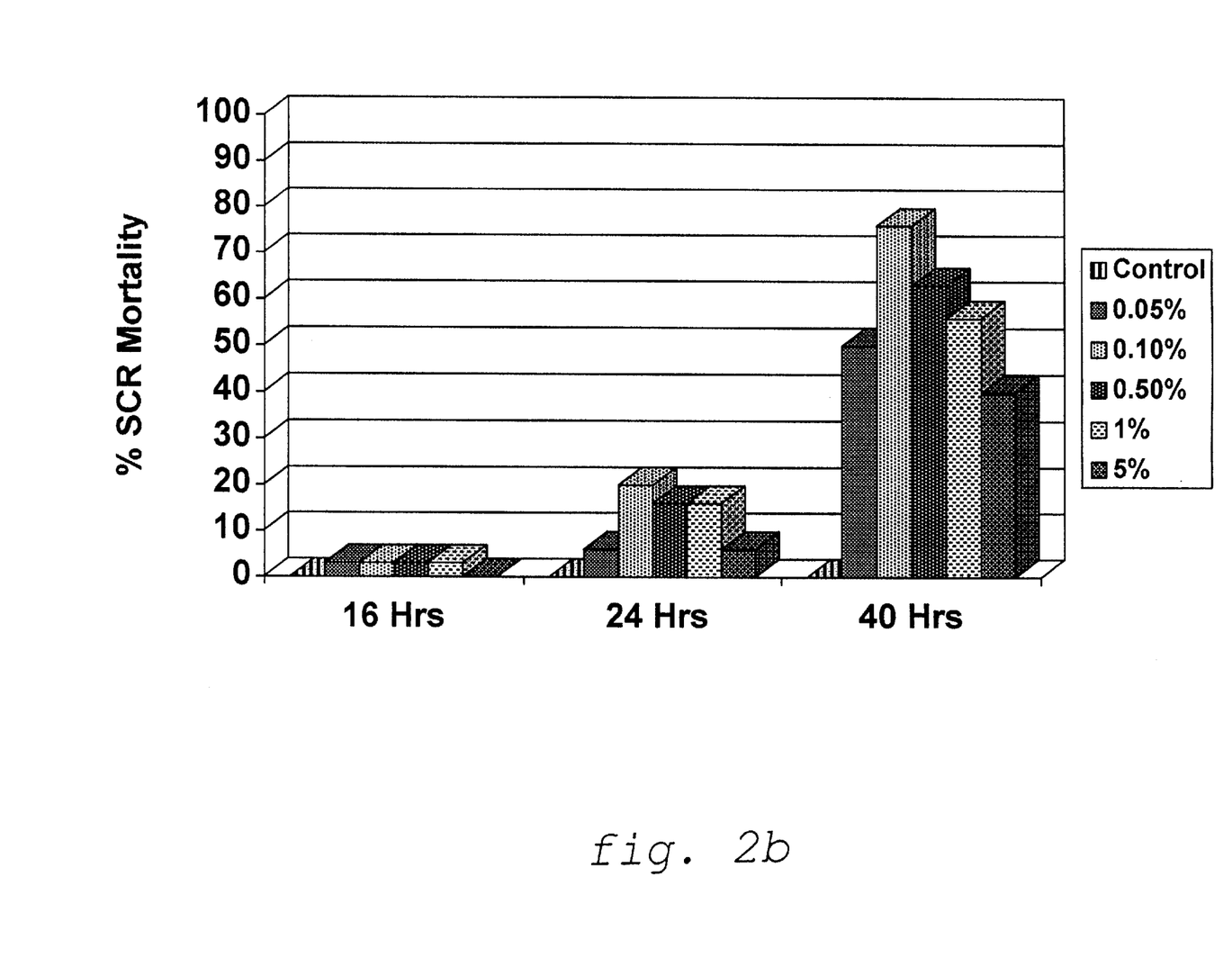
Figure 3:
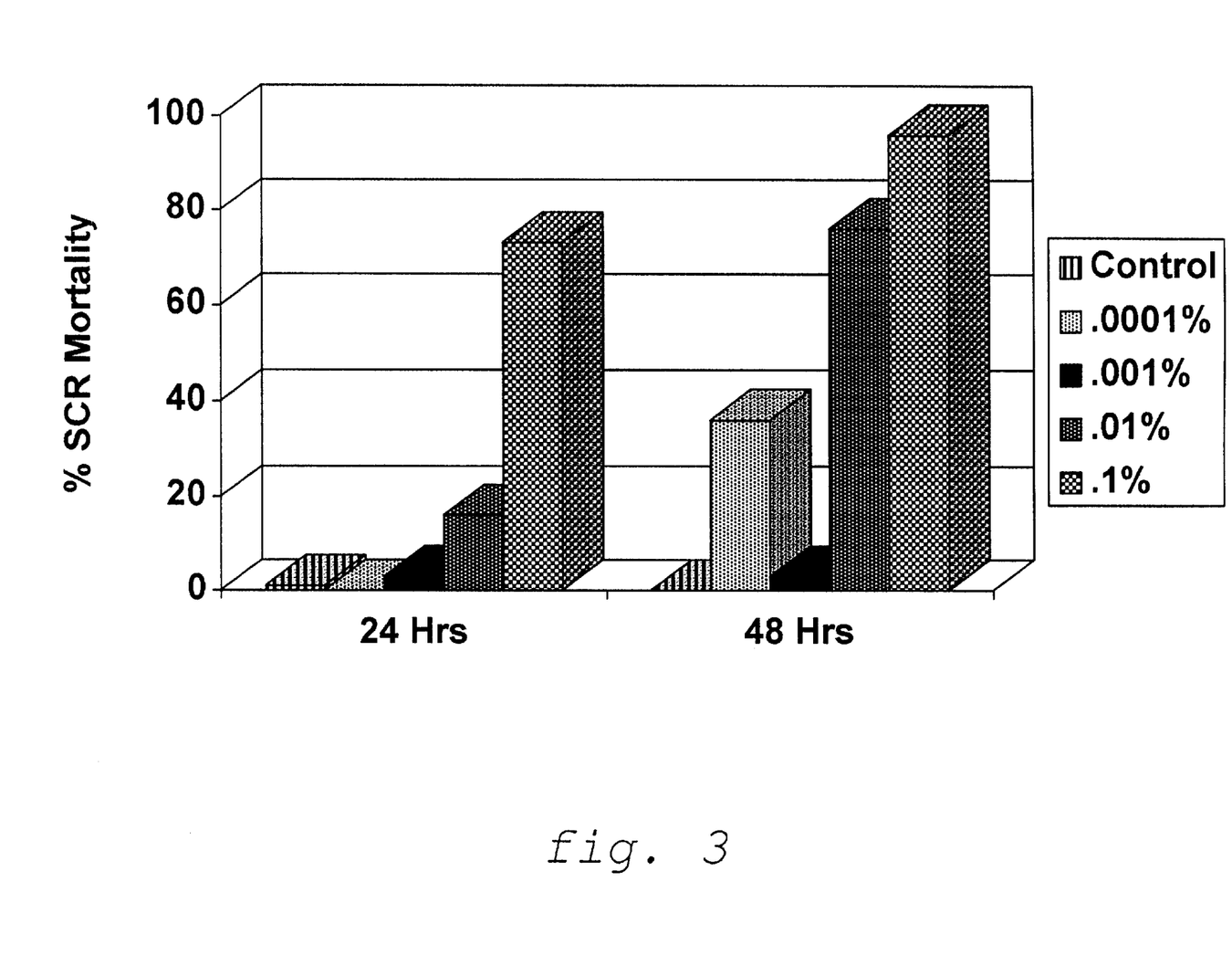
FIG. 3 shows the effects of varying concentrations of dye on SCR mortality when exposed to fluorescent light.
Figure 4:
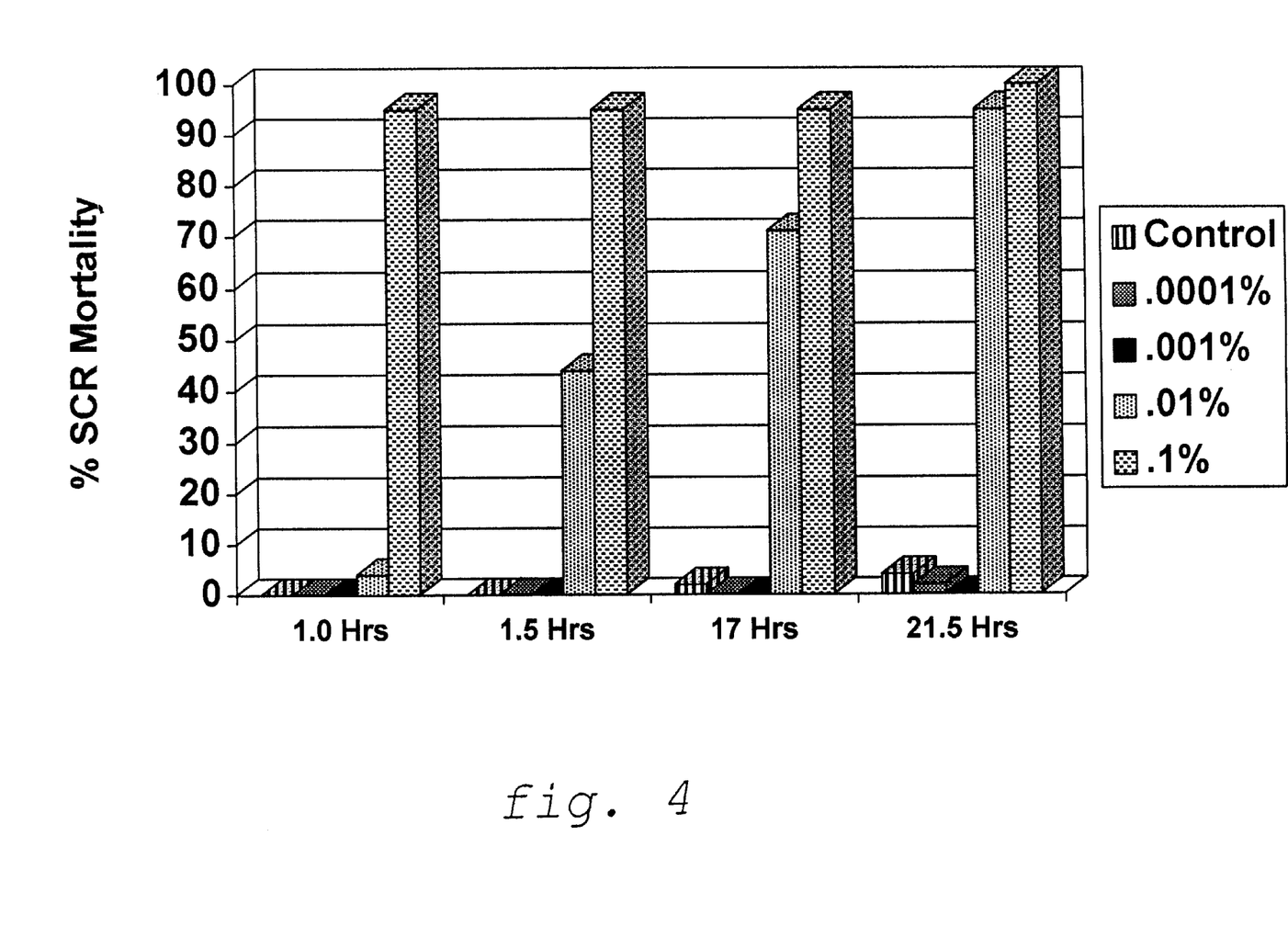
FIG. 4 shows the effects of varying concentrations of dye on SCR mortality when exposed to sunlight.

A water-soluble toxicant was required in order for the toxicant not only to be evenly distributed over the area intended for treatment but also to present a food more palatable to the insect. Various toxicants were studied, and xanthene-type dyes were found to meet the requirements for solubility and efficacy. Photoactive xanthene-type dyes exhibited particularly desireable properties due to activation of toxicity upon exposure to visible light. Fluorescein and the fluorescein derivatives proved especially useful, with the halogenated fluoresceins being preferred. Useful dyes include but are not limited to rose bengal, phloxine B, erythrosin B and eosin. It was also found that more than one dye may also be used in combination. Xanthene-type dyes are considered those dyes having xanthene as the basic structure with substituents which confer the photoactive property.

While not wishing to be bound by theory, it is believed that light-activated toxicity involves a transfer of energy, causing cellular damage which is lethal to the insect (Heitz, J. R. 1982. In: *Insecticide mode of action*. Academic Press, Inc., herein incorporated by reference). The degree of halogenation of the parent fluorescein compound enhances light-activated toxicity. In addition, the dyes affect the insects from a developmental standpoint to some degree, and halogen content appears to play a role in this effect.

Environmentally, the xanthene-type dyes are relatively benign since they are generally non-toxic to non-target organisms, and they have a relatively short lifetime due to photodegradation.

In order to ensure that a sufficient amount of the dye is ingested by the insect, the addition of a feeding stimulant to the insecticidal composition is important. Although cucurbitacins were previously used mostly in dry formulations, they were known to be particularly effective feeding stimulants. Studies were thus carried out to determine if they retained effectiveness when used in combination with the water-soluble photoactive dyes. Experiments were conducted to 1) confirm the advantage of the presence of feeding stimulant, 2) determine an effective concentration range of dye and feeding stimulant and 3) investigate the effects of light on the efficacy of the insecticidal composition.

Initial studies tested dye concentrations in the presence and absence of feeding stimulant and with a starch thickener. Groups of SCR were exposed up to 24 hours to solutions containing dye alone, feeding stimulant alone or a combination of both dye and feeding stimulant (FIG. 1). Results at 24 hours showed a significantly higher number of dead adults present in the group exposed to the combination of dye and feeding stimulant (80%) than either the dye group (15%) or the feeding stimulant group (3%).

Various concentrations (from about 0.05% to about 5%) of dye were also tested against the SCR with (FIG. 2*a*) and without (FIG. 2*b*) the feeding stimulant. Results at 24 hours (FIG. 2*a*) indicate significant increases in dead adults even at the lowest concentration (0.05%) tested. In tests without the feeding stimulant, mortality was less than 20%. Mortality here is due to the normal feeding behavior of the beetle whereby it will eventually need food and feed compulsively on the starch/dye combination and die, as shown in FIG. 2*a*. This test confirmed the advantage of using both a photoactive dye and a feeding stimulant in insecticidal formulations for CRW control.

Experiments were also carried out to determine the effect of light intensity on SCR mortality exposed to dye (from 0.0001% to 0.1%). Exposure to fluorescent light (1/10 the intensity of sunlight) caused 70% mortality in 24 hours at 0.1% dye concentrations (FIG. 3). The $LD_{50}$ at 24 hours for adult corn rootworms exposure to dye was calculated at 0.07%.

Since the photoactivation of the dye is directly proportional to light intensity, exposure for 1 hour to direct sunlight caused more than 90% mortality at the 0.1% concentration and by 21.5 hours more than 90% of the beetles were dead at the 0.01% and 0.1% dye concentration. Results are shown in FIG. 4.

Figure 5:
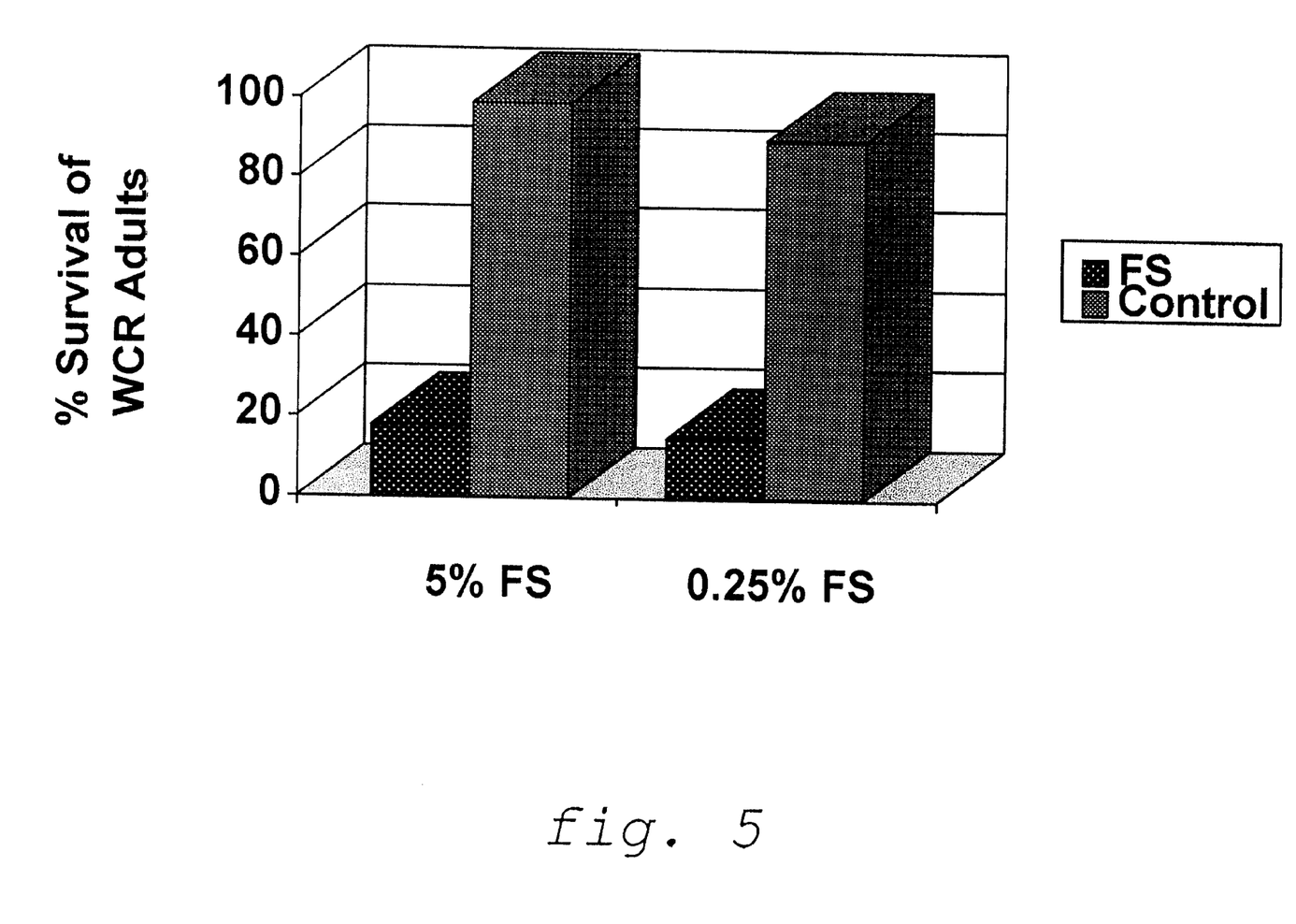
FIG. 5 shows the effects of two different concentrations of feeding stimulant (5% and 0.25%, w/v) and two different exposure time lengths (48 hours and 144 hours, respectively) on western corn rootworm mortality.

Field cage studies were also carried out where corn plants were treated with applications of the insecticidal composition and placed in cages. The composition comprised starch (5%), feeding stimulant (5%), dye (0.06%) and a polymer emulsion (1–3%) to serve as an adherent or sticking agent. An additional cage containing the solution without dye or feeding stimulant served as the control. One hundred fifty WCR adults were released into each cage, exposed to insectidal samples for 48 hours, then removed and counted. Mortality averaged 81% (19% survival) in the treatment cages and 1% (99% survival) in the control cage. In addition, samples of bait which was aged in the field for 6 days caused 83% mortality (17% survival) in laboratory experiments. A subsequent test was carried out where the feeding stimulant concentration was reduced to 0.25% and the exposure period was increased to 6 days. Mortality averaged 85% (15% survival) in the treatment cages and 9% (91% survival) in the control.

It has thus been demonstrated that a composition comprising at least one photoactive xanthene-type dye and a feeding stimulant in aqueous solution is effective as an insecticide against diabroticite beetles. Both larval and adult stages are susceptible to insecticidal activity exhibited by the formulation. The composition may additionally include additives such as adherents of sticking materials, emulsifiers, thickeners, stabilizers, preservatives, antifoam agents and/or buffers. Effective dyes include but are not limited to phloxine B, rose bengal, erythrosin B and eosin, and they may be used alone or in combination. A preferred dye is phloxine B, a xanthene dye registered as D&C (Drug and Cosmetic) Red Dye #28 for use as a color additive in drugs and in cosmetics by the Food and Drug Administration. The dyes are commercially available, e.g. Sure-Dye (Photodye International, Starkville, Miss.).

Cucurbitacins are the recommended feeding stimulant and are known and described in the art for that purpose (see Metcalf et al., 1987, supra; Rhodes et al. 1980. *J. Am. Soc. Hort.* vol. 105, pp. 838–842; Metcalf et al. 1981. *Cucurbit Genet. Coop. Rep.* vol. 4, pp. 37–38; Metcalf, R. L. 1985. *Bull. Ill. Natl. Hist. Surv.* vol. 33, pp. 175–198; Metcalf and Rhodes, Canadian Patent 1,195,922, 1985; How et al. *Environmental Entomol.* vol. 5, pp. 1042–1048, all herein incorporated by reference). The compounds may be obtained by extraction from Cucurbitaceae plants. The plant material may be dehydrated, then ground into a powdery material, or it may be ground up, the solid material filtered off and the filtrate utilized. The bitter mutant of hawkesbury watermelon (BHW), *Citrullus vulgaris* Schrad, is an example of a plant material which containing cucurbitacins which are effective as a feeding stimulant. The melon may be ground to a pulp and the juice extracted. The extraction may be carried out under pressure as in a cider or hydraulyic press, then filtered and utilized directly as a crude liquid extract. It may also be frozen for long-term storage (i.e. months). The juice can also be concentrated by evaporation, spray-drying, freeze-drying or other means to about 3–6% initial weight. Alternatively, cucurbitacins are commercially available, although they are at present somewhat expensive. Although the cucurbitacins are generally used as a mixture of the various related compounds, investigations have been carried out to determine the most effective. It was found that cucurbitacin E-glycoside was the most abundant cucurbitacin in BHM and had the most powerful effect of the cucurbitacin compounds.

The insecticidal composition is prepared by mixing the feeding stimulant concentrate with water to the desired concentration. An effective feeding stimulant concentration is from about 0.001% to about 10% (w/v). The toxicant is then added with mixing to the feeding stimulant solution. An effective toxicant concentration is from about 0.025% (w/v) to about 5% (w/v) of aqueous solution. The various additives may also be mixed into the solution at this point. The concentrations of these additives may vary widely, depending on the requirements necessitated by climate, temperature, field conditions, application method, etc., and these amounts are easily determined by one of skill in the art. For example, a useful formulation may be prepared by combining a crude extract of the BHM at a concentration of from about 0.001% to about 10% (w/v) with phloxine B at a concentration of about 0.0003% to about 0.01%. [NOTE: The phloxine B concentration could vary according to the application method. For example, a concentration of about 0.0003% to about 0.002% (w/v) in a volume of 20 gal/acre applied in an aqueous solution by conventional spray equipment, such as tractor-mounted boom sprayers, backpack sprayers, etc. would be effective, while a concentration of about 0.002% to about 0.01% (w/v) in a volume of 4 gal/acre would be effective for aerial application.] A water soluble starch or other thickening agent, such as Mira Sperse 626 (A. E. Staley Mfg. Co., Decatur, Ill.) may be added at a concentration of from about 1% to about 5% (w/v), and a sticker such as Gelva (Monsanto Corp, St. Louis, Mo.) may be added at a concentration of from about 1% to about 3% (w/v).

The composition is applied to target plants (corn, curcubits, peanuts and other agricultural crops attacked by the CRW) by conventional spraying means. It is applied to cucurbits, for example, at the first sign of CRW adults, usually at the early seedling stage. Treatments are applied weekly for about 3 weeks or until adult CRW populations decline below economic injury levels. In corn, treatment may begin at first evidence of adults present on corn or at the time of silking. Weekly treatments continue for about 3 weeks or until the population of adults declines below the economic injury levels. Trap collections and/or counts of living and dead beetles in the treated corn may be utilized to estimate population levels.

The following examples are intended only to further illustrate the invention and are not intended to limit the scope of the invention as defined by the claims.

EXAMPLES

Example 1

Effect of Feeding Stimulant and Dye on CRW.

In petri dishes, three replications of 10 SCR (mixed sex) were given either 10% starch and distilled water, 10% starch and 10% feeding stimulant (FS), 10% starch and 5% dye or a combination of 10% starch, 10% FS and 5% dye. The petri dishes were placed in a growth chamber about four inches under lights (5200–5900 lux). At 24 hours, the percent of live adults was determined as follows: starch and water, 100%; starch and FS, 97%; starch and dye, 70%; and starch, FS and dye, 7%.

Example 2

Effects of Varying Dye Concentrations in Aqueous Starch Solutions (With and Without FS) and Different Types of Light.

SCR were exposed to five concentrations of dye (5%, 1%, 0.5%, 0.1% 0.05%) in aqueous starch solutions (1–5%, w/v), both with and without FS in the procedure described in Example 1. At 24 hours, on 0.5% dye the mortality was 83% dead from dye and FS, while it was 6% dead from dye and water.

Using reduced dye concentrations of 0.1%, 0.01%, 0.001% and 0.0001% under the same conditions and with 10% FS, at 24 hours the percent of live adults was 13%, 30%, 97% and 97%, respectively.

Using the reduced dye concentrations with 10% FS and 15 SCR per petri dish, dishes were exposed to direct sun (about 72–95,000 lux) for a total of 2½ hours. At 24 hours, the percent of live adults was 0.2%, 100% and 98%, respectively.

Example 3
Choice Test with Variable and Reduced Concentrations of FS.

In a choice test, adult WCR (5♂ and 5♀) were placed in petri dishes containing a treatment ball of 10% starch, 0.06% dye and one of 7 concentrations of FS and a dye-free, FS-free ball. The FS concentrations tested were 5%, 4%, 3%, 2%, 1%, 0.5% and 0.25%. Two FS-free controls were utilized: control 1 having a starch only and a starch/dye ball, and control 2 having 2 starch only balls. Each treatment was replicated 3 times. All dishes received 30-min exposure to direct sun (106,000–63,500 lux). At all other times, dishes were kept 18 inches under fluorescent lamps. At 24 hours, the percent of live adults at 5%, 4%, 3%, 2%, 1%, 0.5%, 0.25%, control 1 and control 2 was 0, 3%, 0, 3%, 0, 3%, 3%, 83% and 97%, respectively.

Example 4
Field Cage Study on Corn.

An insecticidal composition containing 0.25% FS and 0.06% dye was prepared according to the following procedure: 0.12±0.001 g phloxine B (SureDye, PhotoDye International, supra), 20 ml Gelva multipolymer emulsion (Monsanto, supra) and 10 ml of a 5% (w/v) solution containing crude extract of BHM (*Citrullus vulgaris* Schrad) were added with stirring to 60 ml distilled water in a 250-ml beaker. Ten grams of starch (Mira-Sperse 626, supra) was added and mixed thoroughly. Additional distilled water was added to bring the volume up to 200 ml. An additional 100 ml of the above mixture without the dye and FS was also prepared.

Four 6'×6' field cages were assembled and placed in plots of sweet corn. Cages 1, 2 and 3 contained 16, 19 and 16 plants, respectively. Control cage 4 contained 18 plants. Approximately 150 one-week-old WCR adults (75 each of ♂ and ♀) were released into the cages. The mixtures were applied to the plants enclosed inside the cages using a Spraymaster, a chemically-resistant high-volume adjustable hand sprayer (Consolidated Plastics Co., Inc., Twinsburg, Ohio). Each plant was sprayed along the stem, from the mid-point of the plant upward. Approximately 50 ml of the mixture was applied in each cage. The application was carried out at approximately 1:00 P.M., at a temperature of about 86° F., on a sunny day. Light readings were taken at the time of release of the beetles with an Extech Instruments light meter: at tassel height, the light intensity measured 56,500 lux inside the cage and 99,00 lux outside.

At six days post-treatment, beetles were collected from the cages and counted. On each plant the tassels were bent over and shaken, and all leaves pulled down to expose and dislodge any hidden WCR. Mortality averaged 85% in the treated cages and 9% in the control.

We claim:

1. An insecticidal composition comprising a toxicant and a feeding stimulant in an aqueous solution in amounts effective for the control of Diabroticite insects, wherein said toxicant is a xanthene dye selected from the group consisting of phloxine B, rose bengal, erythrosin B and eosin, and said feeding stimulant is a cucurbitacin-containing material.

2. The insecticidal composition of claim 1, wherein said xanthene dye is phloxine B.

3. The insecticidal composition of claim 1, wherein said composition further comprises at least one additive selected from the group consisting of adherents, thickeners, emulsifiers, stabilizers, preservatives, anti-foam agents and buffers.

4. The insecticidal composition of claim 1, wherein said toxicant is present in an amount from about 0.025% (w/v) to about 5% (w/v) of aqueous solution.

5. The insecticidal composition of claim 4, wherein said toxicant is present in an amount from about 0.1% (w/v) to about 0.5% (w/v) of aqueous solution.

6. The insecticidal composition of claim 1, wherein said feeding stimulant is present in an amount from about 0.001% (w/v) to about 10% (w/v).

7. The insecticidal composition of claim 6, wherein said feeding stimulant is present in an amount of from about 1% (w/v) to about 5% (w/v).

8. The insecticidal composition of claim 1, wherein said composition further comprises a thickener and wherein said thickener is a starch.

9. The insecticidal composition of claim 1, wherein said composition further comprises an adherent.

10. The insecticidal composition of claim 1, wherein said composition further comprises an adherent and a thickener, wherein said thickener is a starch.

11. The insecticidal composition of claim 1, wherein said Diabroticite insects are corn rootworms.

12. A method for the control of Diabroticite insects, said method comprising applying a sufficient amount of an insecticidal composition to control said insects, wherein said insecticidal composition comprises a toxicant and a feeding stimulant in an aqueous solution in amounts effective for the control of Diabroticite insects, wherein said toxicant is a xanthene dye selected from the group consisting of phloxine B, rose bengal, erythrosin B and eosin, and said feeding stimulant is a cucurbitacin-containing material.

13. The method of claim 12, wherein said photoactive xanthene dye is phloxine B.

14. The method of claim 12, wherein said insecticidal composition further comprises at least one additive selected from the group consisting of adherents, thickeners, emulsifiers, stabilizers, preservatives, anti-foam agents and buffers.

15. The method of claim 12, wherein said insecticidal composition further comprises a thickener and wherein said thickener is a starch.

16. The method of claim 12, wherein said insecticidal composition further comprises an adherent.

17. The method of claim 12, wherein said insecticidal composition further comprises and adherent and a thickener, wherein said thickener is a starch.

18. The method of claim 12, wherein said Diabroticite insects are corn rootworms.

* * * * *